(12) United States Patent
Bouzid

(10) Patent No.: US 7,286,232 B2
(45) Date of Patent: Oct. 23, 2007

(54) FLUORESCENCE FILTERING SYSTEM AND METHOD FOR MOLECULAR IMAGING

(75) Inventor: Ahmed Bouzid, Lincoln, NE (US)

(73) Assignee: Li-Cor, Inc., Lincoln, NE (US)

( * ) Notice: Subject to any disclaimer, the term of this patent is extended or adjusted under 35 U.S.C. 154(b) by 0 days.

(21) Appl. No.: 11/355,848

(22) Filed: Feb. 15, 2006

(65) Prior Publication Data

US 2007/0188760 A1   Aug. 16, 2007

(51) Int. Cl.
*G01N 21/25* (2006.01)
(52) U.S. Cl. ...................................... 356/417
(58) Field of Classification Search ................. 356/417
See application file for complete search history.

(56) References Cited

U.S. PATENT DOCUMENTS

| | | | | |
|---|---|---|---|---|
| 3,641,344 | A * | 2/1972 | Markle | 356/307 |
| 5,206,699 | A * | 4/1993 | Stewart et al. | 356/30 |
| 6,252,664 | B1 | 6/2001 | Barbera-Guillem | |
| 2001/0028458 | A1* | 10/2001 | Xiao | 356/417 |
| 2003/0007254 | A1* | 1/2003 | Tocci | 359/663 |
| 2005/0151972 | A1* | 7/2005 | Boege et al. | 356/417 |

OTHER PUBLICATIONS

Hwang et al., "The influence of improved interference filter performance for molecular imaging using frequency domain photon migration measurements," Optical Tomography and Spectroscopy of Tissue VI, SPIE vol. 5693, pp. 503-512, Apr. 2005.
Hwang et al., "Enhanced fluorescent optical imaging with improved excitation light rejection," presented at the Fourth Annual Meeting of the Society for Molecular Imaging (SMI) on Sep. 7-10, 2005 in Cologne, Germany, 1 page.
Lichtman et al., "Fluorescence microscopy," Nature Methods 2, pp. 910-919, Nov. 18, 2005.
Xenogen Product Sheet: IVIS® Imaging System 200 Series, 2004, 4 pages.
"Product Listing: IRDye™ Infrared Dyes," http://www.licor.com/bio/IRDyes/PL-IRDyes800CW.jsp, 1 page (2005).
"Fluorescence Spectraviewer," http://probes.invitrogen.com/resources/spectraviewer/, 1 page (printed Feb. 9, 2006).

* cited by examiner

*Primary Examiner*—Gregory J. Toatley, Jr.
*Assistant Examiner*—Kara Geisel
(74) *Attorney, Agent, or Firm*—Townsend and Townsend and Crew LLP

(57) ABSTRACT

An optical system is disclosed that can be used for fluorescence filtering for molecular imaging. In one preferred embodiment, a source subsystem is disclosed comprising a light source and a first set of filters designed to pass wavelengths of light in an absorption band of a fluorescent material. A detector subsystem is also disclosed comprising a light detector, imaging optics, a second set of filters designed to pass wavelengths of light in an emission band of the fluorescent material, and an aperture located at a front focal plane of the imaging optics. A telecentric space is created between the light detector and the imaging optics, such that axial rays from a plurality of field points emerge from the imaging optics parallel to each other and perpendicular to the second set of filters.

22 Claims, 8 Drawing Sheets

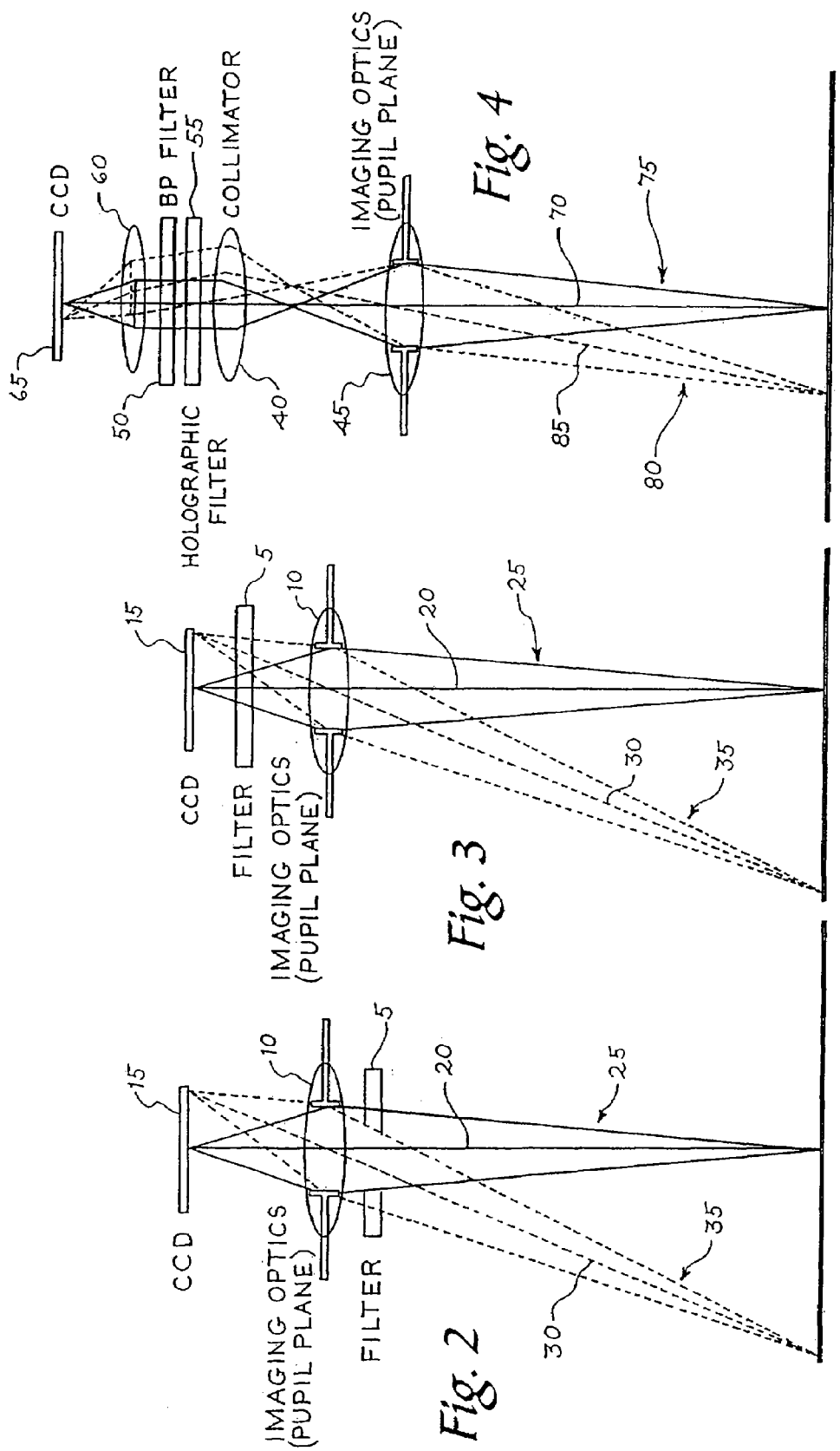

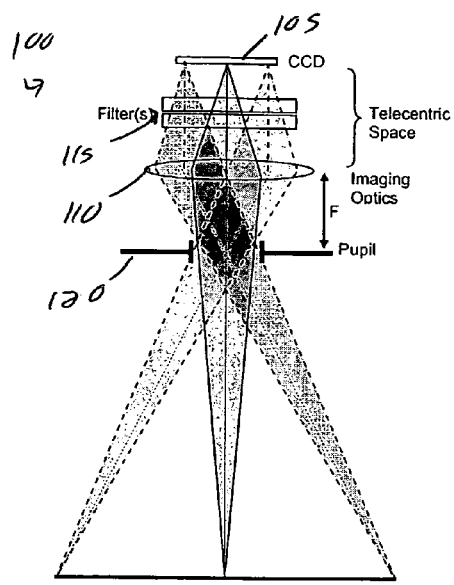
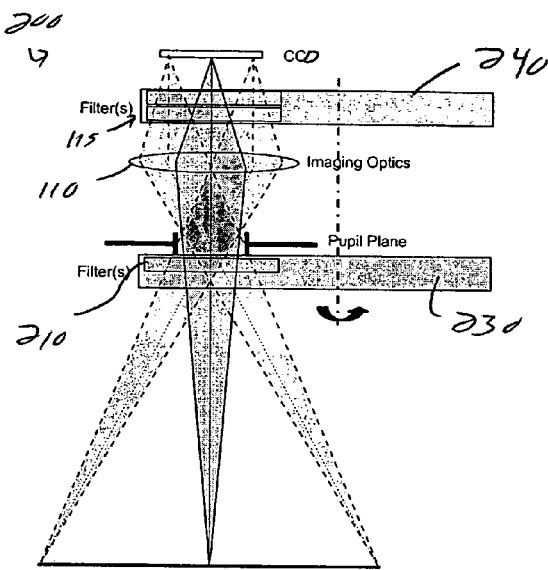
Figure 5
Figure 6
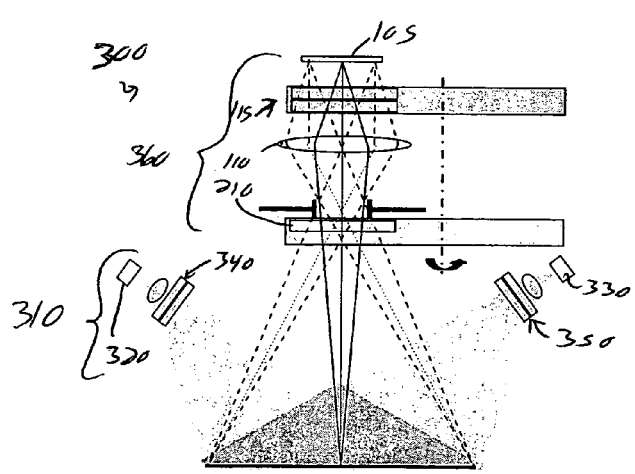
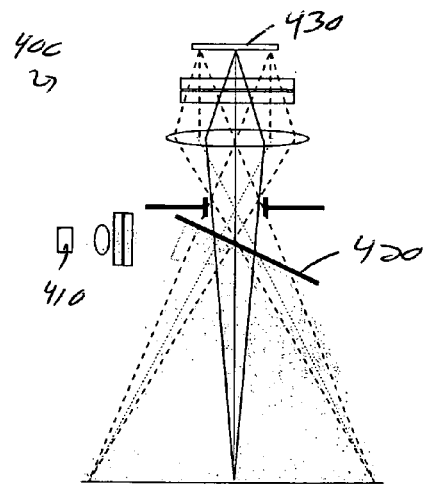
Figure 7
Figure 8

FLUORESCENCE FILTERING SYSTEM AND METHOD FOR MOLECULAR IMAGING

BACKGROUND

A fluorescence optical system illuminates a fluorophore-labeled target with light whose wavelength content falls within the absorption band and collects light whose wavelength content is in the emission band. An emission filter placed in front of a detector filters light that is not in the emission band. One challenge with emission filters is that unwanted photon rejection depends on the angle at which light traverses the filter. Specifically, as the angle of incidence increases, the transmission/reflection of the filter shifts to lower wavelengths. Accordingly, even if the field of view is a single point that provides an axial ray at a 0 degree angle, other rays of the same light beam will pass through the filter at non-0 degree angles and, accordingly, may experience different amounts of filtering.

This situation is addressed in Hwang et al., "The influence of improved interference filter performance for molecular imaging using frequency domain photon migration measurements," Optical Tomography and Spectroscopy of Tissue VI, SPIE vol. 5693, pp. 503-512. Hwang et al. describes an optical system in which a collimator is placed between imaging optics and an emission filter. The collimator ensures that all rays in a light beam originating from a certain point in the image field will pass through the filter at a 0 degree angle and, thus, will receive the same type of filtering. However, if a relatively large field of view is used, light beams emanating from the edge of the field, while still collimated, will pass through the filter at an angle. This results in different amounts of excitation leakage across the field.

There is a need, therefore, for a fluorescence filtering method and system that will overcome this problem.

SUMMARY

The present invention is defined by the following claims, and nothing in this section should be taken as a limitation on those claims.

By way of introduction, the preferred embodiments described herein relate to an optical system that can be used for fluorescence filtering for molecular imaging. In one preferred embodiment, a source subsystem is disclosed comprising a light source and a first set of filters designed to pass wavelengths of light in an absorption band of a fluorescent material. A detector subsystem is also disclosed comprising a light detector, imaging optics, a second set of filters designed to pass wavelengths of light in an emission band of the fluorescent material, and an aperture located at a front focal plane of the imaging optics. A telecentric space is created between the light detector and the imaging optics, such that axial rays from a plurality of field points emerge from the imaging optics parallel to each other and perpendicular to the second set of filters. Other preferred embodiments are provided, and each of the preferred embodiments described herein can be used alone or in combination with one another.

The preferred embodiments will now be described with reference to the attached drawings.

BRIEF DESCRIPTION OF THE DRAWINGS

FIG. 2 is an illustration of an optical arrangement in which an emission filter is placed in front of imaging optics.

FIG. 3 is an illustration of an optical arrangement in which an emission filter is placed between the imaging optics and a detector.

FIG. 4 is an illustration of an optical arrangement using a collimator.

FIG. 5 is an illustration of a detector system of a preferred embodiment.

FIG. 6 is an illustration of a detector system with a filter wheel of a preferred embodiment.

FIG. 7 is an illustration of a fluorescence filtering system of a preferred embodiment.

FIG. 8 is an illustration of a fluorescence filtering system of another preferred embodiment.

DETAILED DESCRIPTION OF THE PRESENTLY PREFERRED EMBODIMENTS

Figure 1B:
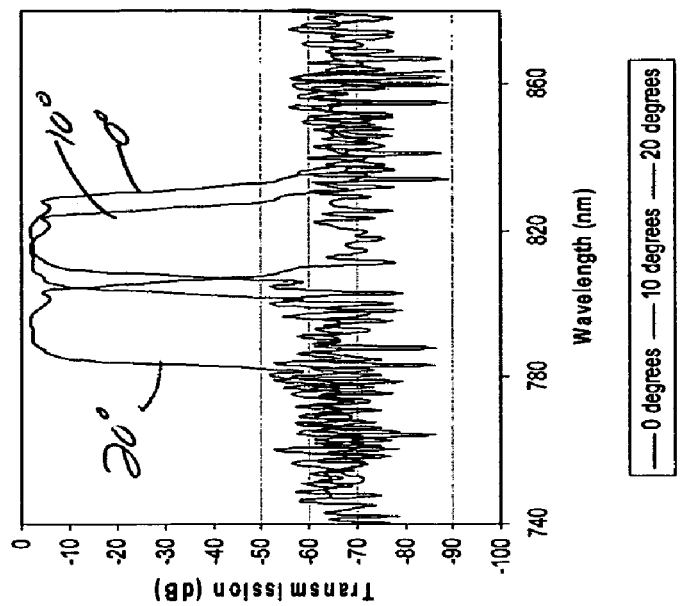
FIGS. 1A and 1B are graphs showing wavelength shifting of a band-pass filter due to incident angular variation.

Fluorescence detection is a tool for molecular imaging. It enables researchers to detect particular components of complex bio-molecular assemblies, such as in live cells. Fluorescence is a photo-physical process that involves the interaction of light with certain molecules called fluorophores or fluorescent dyes. It consists of the absorption of light energy at the appropriate wavelength by such molecules and the subsequent emission of other light photons at longer wavelengths. The wavelength ranges that a fluorophore molecule can absorb and emit at are called absorption and emission bands, respectively.

A fluorescence optical system illuminates a fluorophore-labeled target with light whose wavelength content falls within the absorption band and collects light whose wavelength content is in the emission band. The source(s) and optics that generate the illumination part of the system are called the "excitation optics," and the optics used to collect the fluorescence emission are called the "emission optics." Since it is rarely possible to find a light source that has a spectral content (i.e., wavelength range) that exactly matches every fluorophore absorption band, special optical filters (usually band-pass filters) are used along with the light sources to limit the range of illuminating wavelengths to that of the absorption band and not the emission band. At the same time, other filters are used in the emission path to allow light with wavelengths in the emission band only to reach the detector.

The task of a fluorescence optical system design is to make sure that photons with wavelengths in the absorption band only reach the target, and photons with wavelengths in the emission band only reach the detector. If not, photons from the light source will wrongly be considered as fluorescence, and, therefore, a wrong measure of the amount of fluorophore dye results. This can be a tough task if the amount of emitted fluorescence is much less than the amount of excitation light scattered by the target surface (i.e., not absorbed). This is usually the case for in-vivo imaging, such as in small animal imaging, since there are a number of challenges to achieving good signal-to-noise performance when imaging fluorescence targets deep inside small animals.

One challenge is that the amount of excitation light that reaches the inside of an animal is usually quite low because of the significant absorption and scattering caused by the various body parts (skin, muscle, fat, bone, etc.). For example, the transmission through "shaved skin+fat layer+whole rib cage+abdominal wall" is in the order of $10^{-6}$ and varies with the thickness and composition of each of those parts. The emitted fluorescence will have to traverse a comparable tissue path back up towards the detection system. Thus, the level of fluorescence is $<<10^{-12}$ times that of the excitation signal. So, for example, if a flux density of 1 mW/cm$^2$ impinges upon the outside of a mouse or other small animal, only a sub-nano Watt optical signal actually reaches dye-labeled cells inside the abdomen, and, in turn, only sub-femto Watt of fluorescence signal reaches the detector. The low amount of emitted fluorescence is further reduced by absorption and scattering as it makes its way out towards the detector. This means that the scattering from the excitation light that occurs at the outer parts of the animal can cause much higher levels than the fluorescence signal itself. At the same time, existing optical filter technology (e.g., thin-film emission filters, such as multi-cavity designs) can, at best, provide rejection of unwanted photons only in the order of OD6 ($10^{-6}$). So, standard fluorescence methods would allow through high non-fluorescent background levels and, in turn, result in low Signal-to-Background (SBR) and Signal-to-Noise (SNR) ratios.

Another challenge is that unwanted photon rejection also depends on the angle at which light traverses the filter, as the spectral properties of optical thin film filters vary with the angle of incidence of light. Specifically, as the angle of incidence increases, the transmission/reflection of the filter shifts to lower wavelengths ("blue shift"). This shift can be described by $$\lambda(\theta) = \lambda_o \sqrt{1 - (\sin\theta/\bar{n})^2}$$

where $\theta$ is the angle deviation from the normal to the filter, and $\bar{n}$ is the effective index of refraction of the thin-film. The value of $\bar{n}$ is typically in the range of 1.5 to 2.5 and varies with polarization.

Figure 1A:
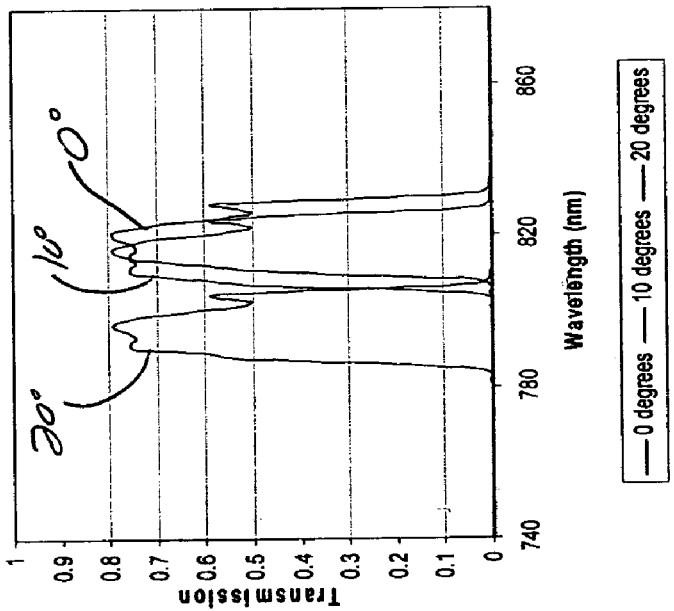

FIGS. 1A and 1B are graphs (transmission and transmission (dB), respectively) showing wavelength shifting of a band-pass filter due to a varying angle of incidence (0, 10, and 20 degrees). As shown in these graphs, as the angle of collected light increases relative to the normal to the filter, the effective transmission band shifts to lower wavelengths, and the amounts of transmitted fluorescence and background signals change accordingly. Light from the target spans a significant range of field angles when a relatively large field of view is imaged, such as in the case of small animal imaging. Therefore, in small animal imaging where a relatively large field of view is imaged, the resulting emission filtering (i.e., transmitted SBR) is non-constant across the image. Accordingly, it is desired to use special spectral filtering solutions in order to improve the rejection of non-fluorescence light across the whole field of view (i.e., where light is collected at different angles).

Many current area fluorescence imaging techniques use the same excitation and emission filters designed for microscopy and scanning systems and use arrangements where the emission filter 5 is placed in front of the imaging optics 10 (as in FIG. 2) or behind it (as in FIG. 3, where the emission filter 5 is between the imaging optics 10 and the detector 15 (here, a CCD)). (The horizontal lines from which the emission is originating in these and other figures herein represent a target, such as mouse or other small animal.) These filters are typically multi-cavity interference filters optimized for maximum rejection in the excitation band and maximum transmission in the emission band. As discussed earlier, the spectral properties of such filters vary with the angle of incidence of light. Because, in FIG. 2, the axial ray 20 (i.e., the "chief" or center ray of a light beam) of light beam 25 is at a 0 degree angle to the filter 5, while the axial ray 30 of light beam 35 is at about a 45 degree angle to the filter 5, the filter 5 will provide different photon rejection characteristics of the axial rays 20, 30. This is also true in the arrangement in FIG. 3. In FIG. 3, the filter 5 is behind the imaging optics 10. Because the pupil plane (i.e., the plane at which axial rays of all light beams cross) is in the center of the imaging optics 10, the axial ray passes through the imaging optics 10 without changing direction. Accordingly, the filter 5 in FIG. 3, like the filter 5 in FIG. 2, will provide different photon rejection characteristics of the axial rays 20, 30. Accordingly, in both arrangements, the angular spectral dependence of the filter 5 results in a significant amount of excitation leakage that both limits the achievable SBR and is non-constant across the image.

It should be noted that, even in the instance where the axial ray 20 passes through the filter 5 at a 0 degree angle, other rays of the light beam 25 pass through the filter 5 at a non-0 degree angle. Accordingly, even if the field of view is a single point that provides an axial ray at a 0 degree angle, other rays of the same light beam will pass through the filter 5 at non-0 degree angles and, accordingly, may experience different amounts of filtering by the filter 5 due to the angular spectral dependence problem.

This situation is addressed in Hwang et al., "The influence of improved interference filter performance for molecular imaging using frequency domain photon migration measurements," Optical Tomography and Spectroscopy of Tissue VI, SPIE vol. 5693, pp. 503-512. FIG. 4 is an illustration of the arrangement disclosed in Hwang et al. As shown in FIG. 4, a collimator 40 is placed between imaging optics 45 and band-pass and holographic filters 50, 55. (Hwang suggests the use of a holographic notch filter 55 to enhance the rejection capability of the band-pass filter 50.) A lens 60 focuses the light beams passing through the filters 50, 55 onto a CCD detector 65. The collimator 40 causes the rays of each of the light beams to exit the collimator 40 parallel to each other. As a result, unlike the situation noted above, if the field of view is a single point that provides an axial ray 70 through the filters 50, 55 at a 0 degree angle, other rays of the same light beam 75 will also pass through the filters 50, 55 at a 0 degree angle because of the effect of the collimator 40. However, as shown in FIG. 4, if a relatively large field of view is used, a light beam 80 emanating from the edge of the field, while still collimated, traverses the filters 50, 55 at an angle. This is because the pupil plane is in the center of the imaging optics 45, and the axial ray 85 of light beam 80 passes through the imaging optics 45 without changing direction. Accordingly, light from different field points enter the filters 50, 55 at different angles and, therefore, results in different amounts of excitation leakage across the field.

FIG. 5 is an illustration of a detector system 100 of a preferred embodiment that minimizes field dependence and maximizes the Signal to Background Ratio (SBR) performance of spectral filtering. The detector system 100 comprises a light detector 105 (such as a CCD), imaging optics 110 with an equivalent focal length F, a set of filters 115 positioned between the light detector 105 and the imaging optics 110, and an aperture 120 located at a front focal plane of the imaging optics 110. As used herein, the term "imaging optics" refers to one or more optical elements whose function collectively is to project a scene onto a detector (e.g., a sensor array) such as a CCD camera. Imaging optics can comprise a single lens if its placement allows it to project the picture of a given scene onto the detector. Imaging optics can also comprise two or more lenses together in such a way that they all work together to produce the same function (i.e., project the image of a scene onto a detector). The term "imaging optics" can be used interchangeably with the terms "imaging lens" and "imaging lens assembly." Further, imaging optics can include components other than lenses (e.g., mirrors). As also used herein, a "set" can include one or more than one member. Accordingly, a set of filters, for example, can contain a single filter or a plurality of filters. In this way, one can stack one or more filters to achieve the desired background rejection.

By locating the aperture 120 in front of the imaging optics 110, the pupil plane (i.e., the plane at which axial rays of all light beams cross) is not in the center of the imaging optics 110, and axial rays that hit the imaging optics 110 at non-0 degree angles will change direction when exiting the imaging optics 110. Further, because the pupil aperture 120 located at a front focal plane of the imaging optics 110, the pupil plane is in the front focal plane of the imaging optics 110, and a telecentric space is created between the imaging optics 110 and the light detector 105. This will cause the axial rays from a plurality of field points (i.e., locations in the imaged target) to emerge from the imaging optics 110 parallel to each other and perpendicular (i.e., at a 0-degree angle) to the set of filters 115. (A telecentric approach also eliminates otherwise unavoidable ghost images when the set of filters 115 comprises more than one filter.) As a result, each of the axial rays will receive the same filtering from the set of filters 115. While the non-axial rays of each light beam will hit the set of filters 115 at non-0 degree angles and, hence, be subject to varying filtering effects due to the angular dependence problem, such rays from each light beam will see the same effect. In other words, in the telecentric space, all the field points (light emanating from different parts of the image) traverse the set of filters 115 in the same manner, centered around the zero-degree angle. This minimizes the angular variation across the field and, thus, the resulting spectral filtering variation. Accordingly, unlike with the optical arrangement in FIG. 4, light from different field points entering the set of filters 115 at different angles will result in substantially the same amount of excitation leakage across the field.

FIG. 6 is an illustration of a detector system 200 of another preferred embodiment. This system 200 is similar to the system 100 in FIG. 5, and common components are labeled the same. However, the system 200 in FIG. 6 has an additional set of filters 210 in front of the imaging optics 110. Preferably, the set of filters 210 comprises one or more dichroic filters. This system 200 takes advantage of the fact that rays that traverse a filter placed in front of imaging optics at large angles will traverse a filter placed behind the imaging optics at smaller angles and vise versa. This has the effect of balancing out any residual leakage and, thus, flattening the field. Therefore, by placing the additional set of filters 210 in front of the imaging optics 110, the angular effect from the first set of filters 115 is balanced out more evenly across the field. Although not necessary, the additional set of filters 210 in this embodiment is located on a filter wheel 230 comprising at least one additional set of filters (not shown). Similarly, the set of filters 115 can be placed in a filter wheel 240 comprising at least one additional set of filters (not shown). This allows different "colors" of filters to image different labels.

Turning again to the drawings, FIG. 7 is an illustration of a fluorescence filtering system 300 of another preferred embodiment. This system 300 comprises a source subsystem 310 comprising two light sources 320, 330, each with a set of filters 340, 350 designed to pass wavelengths of light in an absorption band of a fluorescent material. (As discussed above, a filter may leak wavelengths of light in other bands.) The system 300 also comprises a detector subsystem 360, identical to the detector system 200 in FIG. 6 (components are labeled the same). Preferably, rejection performance of the set of excitation filters 340, 350 in the excitation paths matches the rejection performance of the set of emission filters 115. Since the detector 105 responds to all the photons that pass through the excitation as well the emission bands, the rejection by both the set of excitation and emission filters 115, 340, 350 is preferably matched so that leakage from the set of excitation filters 340, 350 in the emission band will have the same effect as a comparable leakage from the set of emission filters 115 in the excitation band. It should be noted that, while FIG. 7 shows two light sources 320, 330, three or more light sources can be used. Also, the number of light sources does not have to match the number of sets of filters. For example, one can use one light source with one filter set and then split the output to act like separate sources. Alternatively, one can split the output to more than one port and put filter sets in front of each port.

FIG. 8 is an illustration of an alternate system 400, in which a single source 410 is used with a dichoric splitter 420. The dichroic splitter 420 is positioned such that light from the light source 410 illuminates a target and light emitted from the target reaches the detector 430. The dichroic splitter 420 also has filtering properties like the set of filters 210 in FIGS. 6 and 7. However, the advantage of using the set of filters 210 in FIGS. 6 and 7 is that they prevents any possible specular reflections from getting into the collection optics.

In one presently preferred embodiment of the system 300 shown in FIG. 7, the detector is a Hamamatsu ORCA_AG detector, the imaging optics 110 is a Canon 50 mm/F2.0 lens, the set of emission filters 115 are Omega 822DF20 filters, and the second set of filters 210 is a Semrock 800LP filter, operating at a nominal zero-degree angle of incidence. The excitation sources preferably consist of two fiber-coupled, symmetrically-positioned identical laser diode sources (782 nm) as the light sources 320, 300 and a set of two excitation filters 340, 350 in front of each laser 320, 330. Both excitation and emission filters have about OD6 rejection each.

Figure 9:
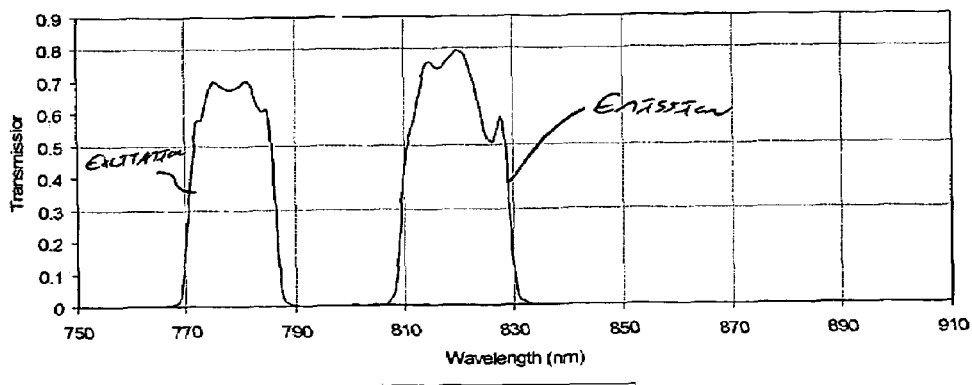
FIG. 9 is a graph of transmission curves for excitation and emission filters of a preferred embodiment.
Figure 10:
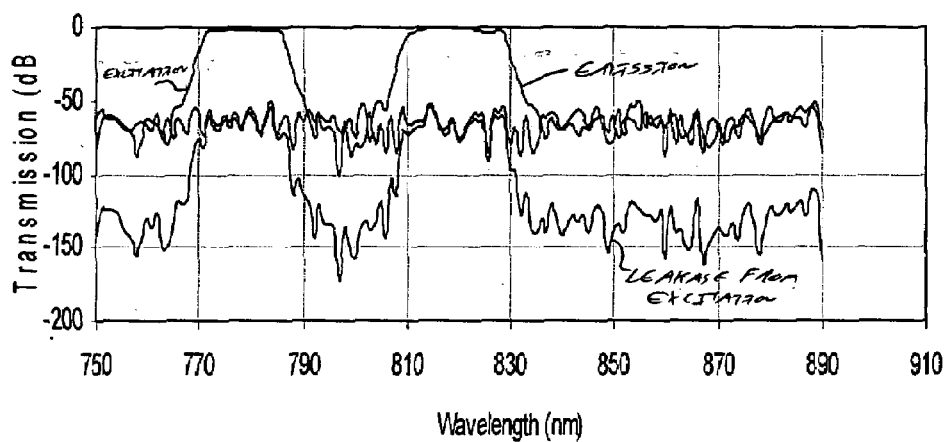
FIG. 10 is a graph showing the same data as in FIG. 9 but in log scale.
Figure 11:
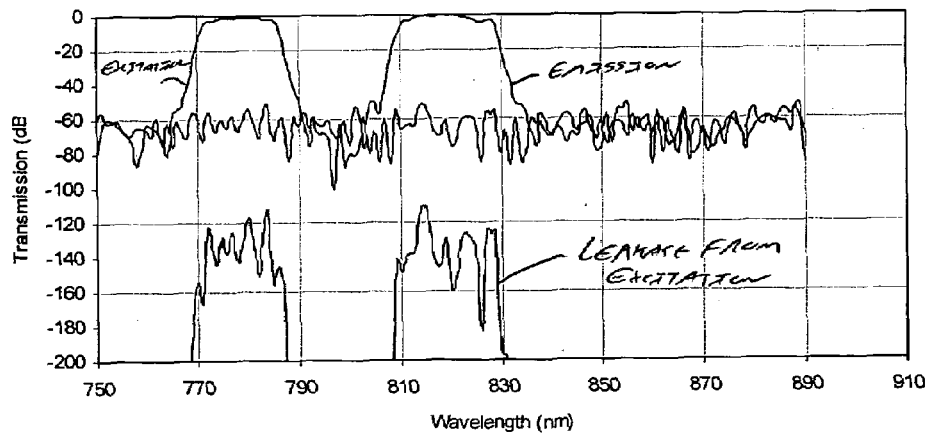
FIG. 11 is a graph showing reduction in residual leakage using the filtering architecture shown in FIG. 7.

Turning again to the drawings, FIG. 9 is a graph showing transmission curves for the excitation and emission filters. FIG. 10 shows the same data in log scale so that the rejection level can be better evaluated. Tests were conducted to confirm that rejection with a configuration of (2, 2) excitation and emission filter sets is better than (1, 1), (1, 2), and (2, 1) configurations. Of course, if further rejection is needed, one can use (3, 3), (4, 4), etc. FIG. 11 is a graph showing reduction in residual leakage from the filtering architecture shown in FIG. 7. A comparison between FIGS. 10 and 11 show the theoretical level of reduction in background leakage that can be achieved by doubling the rejection capability of both the excitation and emission filters.

FIGS. 12-15 show horizontal cross-sections from images obtained with the prototype system described above. The target is a nitro-cellulose membrane with 5 IRDye® 800 labeled fluorescent spots. The membrane produces a significant amount of scattering from the excitation laser and is thus used to obtain a measure of the rejection capability of the filters and the flatness of the residual background. The cross-section is arbitrarily chosen to pass through a fluorescent spot located near the center of the image. Such fluorescent spot is used to measure the fluorescence transmission efficiency. This way, a measure of Signal-to-Background (SBR) can easily be obtained. In each figure, the graph is displayed in log-scale in order to enhance the levels of the background.

Figure 12:
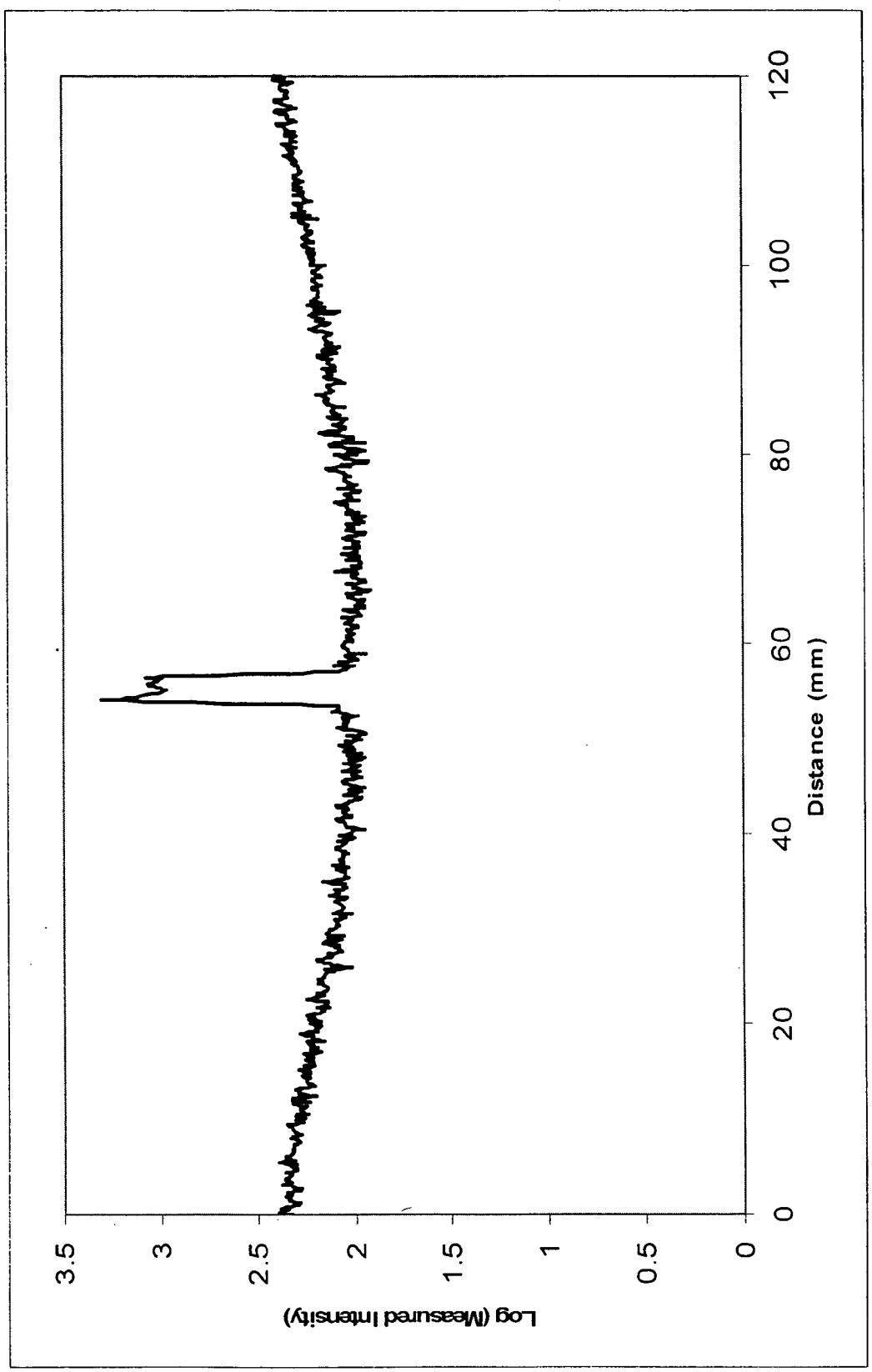
FIG. 12 is a graph showing a horizontal cross-section from a fluorescence image obtained with a prototype system of a preferred embodiment with one band-pass filter placed in front of the lens at T=5 s.
Figure 13:
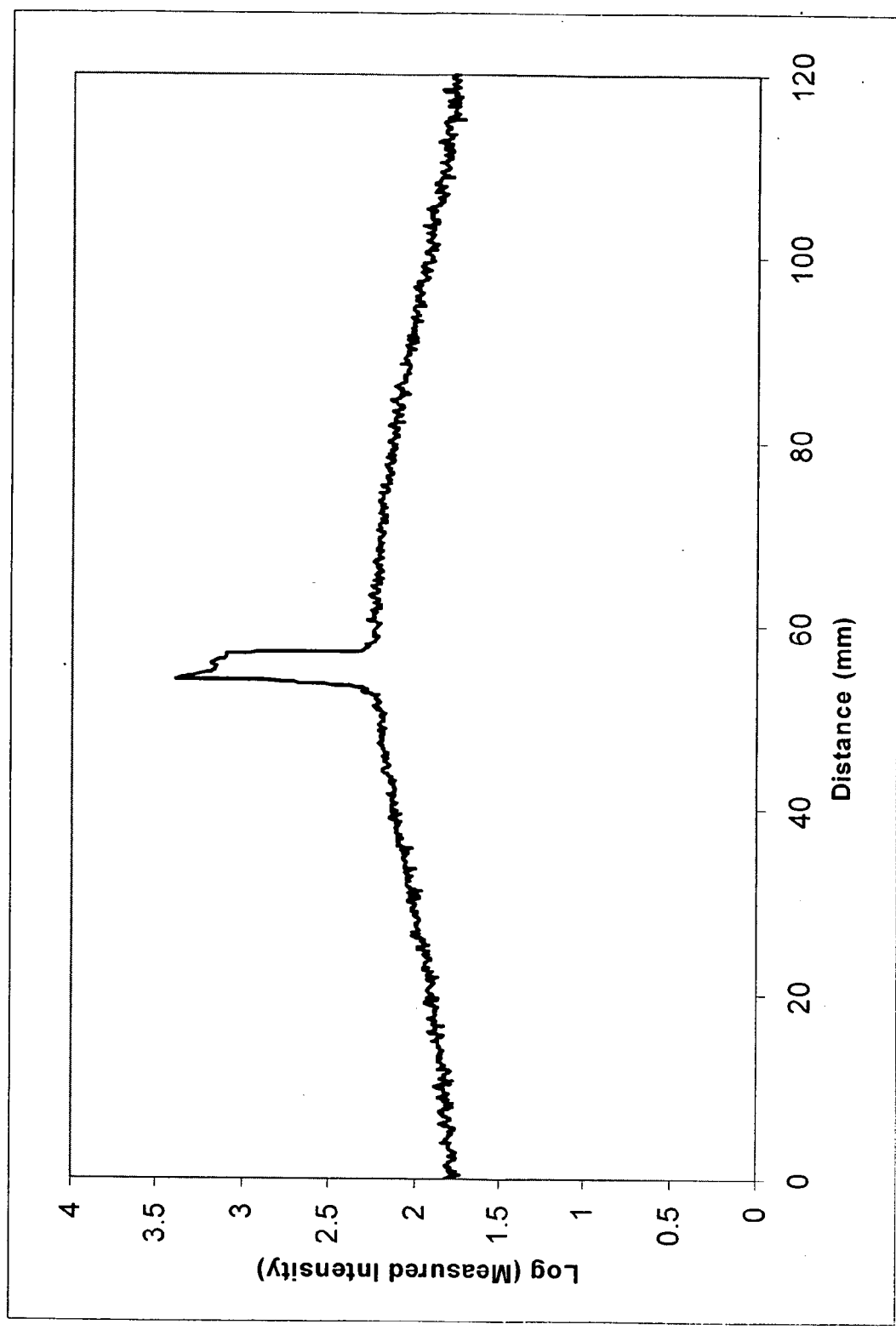
FIG. 13 is a graph showing a horizontal cross-section from a fluorescence image obtained with a prototype system of a preferred embodiment with one band-pass filter placed behind the lens at T=5 s.
Figure 14:
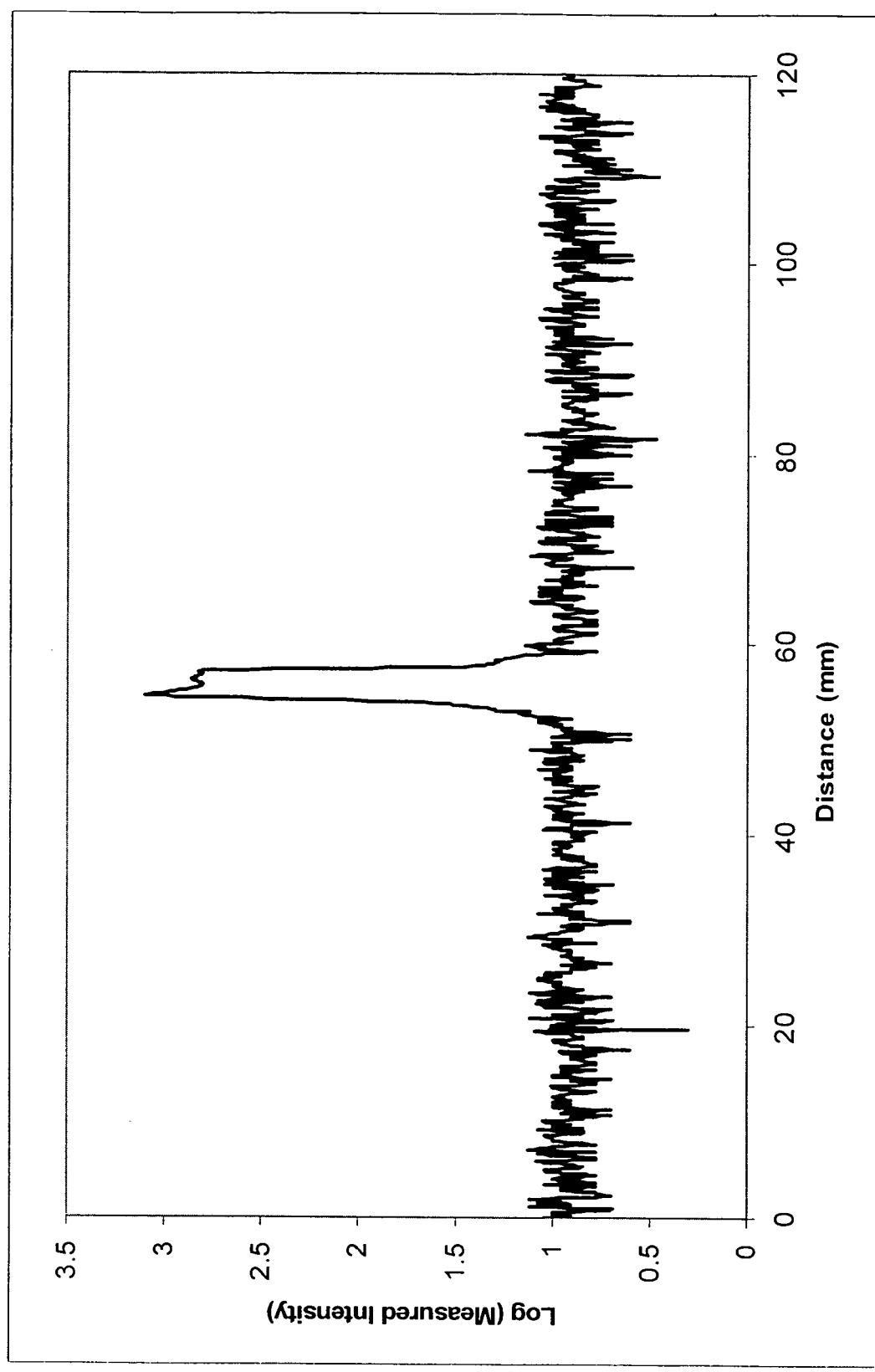
FIG. 14 is a graph showing a horizontal cross-section from a fluorescence image obtained with a prototype system of a preferred embodiment at T=5 s.
Figure 15:
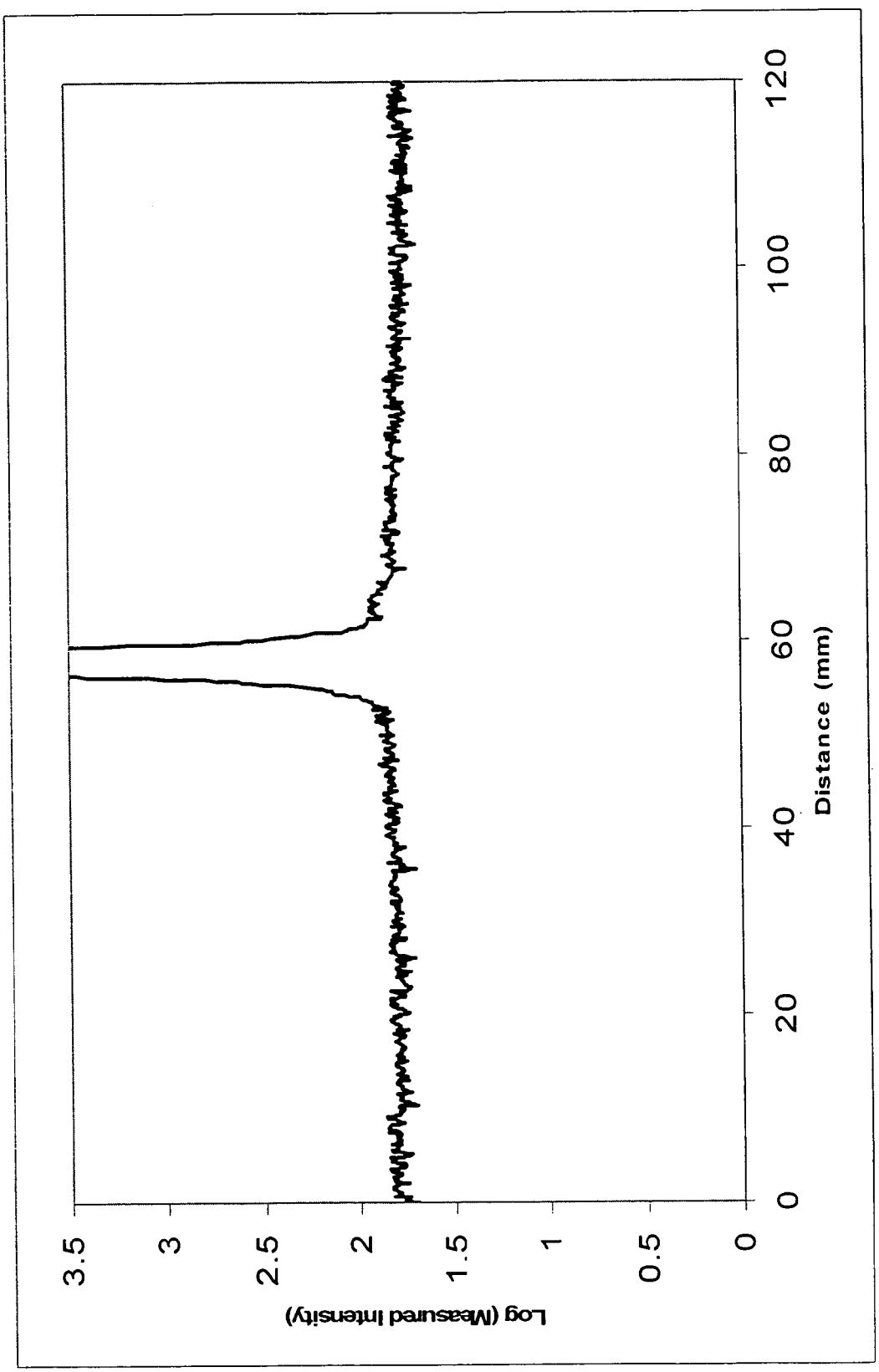
FIG. 15 is a graph showing a horizontal cross-section from a fluorescence image obtained with a prototype system of a preferred embodiment at T=120 s.

In FIGS. 12 and 13, only one emission filter was placed in front and in the back of the lens, respectively. This is similar to what is done in most prior small animal imaging solutions. It also shows how the non-flatness of the background in both cases complements each other, and, therefore, by placing filters on both sides of the lens, a more balanced rejection is obtained. FIGS. 14 and 15 show the image with filters configured according to the preferred embodiment of FIG. 7. In FIG. 15, the exposure time is increased to 120 s in order to enhance the detection of any residual background leakage. As is clear from the image, even though the fluorescent signal is much higher than saturation, the leakage is still flat and non-significant. The SBR improvement in this case is estimated to be ~30×.

There are several alternatives that can be used with these embodiments. For example, while the preferred embodiments have been illustrated above with respect to an application for fluorescence filtering for molecular imaging, these embodiments can be used in an suitable application. Accordingly, the filters do not have to be designed to pass wavelengths of light in absorption and emission bands of fluorescent materials. Also, while these embodiments were illustrated in terms of imaging a small animal, such as a mouse, they can be used to image other targets. Additionally, any suitable light source, detector, filter, imaging optics, and aperture can be used. Further, any of the embodiments disclosed herein can be used by itself or in combination with any of the other embodiments disclosed herein. Finally, each of the excitation filter sets can pass wavelengths in more than one excitation band, and emission filter sets can pass wavelengths in more that one emission band. Also, any of the sets of filters disclosed herein can be placed on a filter wheel.

It is intended that the foregoing detailed description be understood as an illustration of selected forms that the invention can take and not as a definition of the invention. It is only the following claims, including all equivalents, that are intended to define the scope of this invention.

What is claimed is:

1. A fluorescence filtering system comprising:
a source subsystem comprising:
a light source; and
a first set of filters designed to pass wavelengths of light from the light source to a fluorescent material in an absorption band of a the fluorescent material; and
a detector subsystem for detecting light from the fluorescent material comprising:
a light detector;
imaging optics;
a second set of filters positioned between the light detector and the imaging optics, the second set of filters designed to pass wavelengths of light in an emission band of the fluorescent material; and
an aperture located at a front focal plane of the imaging optics, wherein a telecentric space is created between the light detector and the imaging optics, such that axial rays from a plurality of field points emerge from the imaging optics parallel to each other and perpendicular to the second set of filters.

2. The system of claim 1 further comprising a third set of filters, wherein the second set of filters is located on one side of the imaging optics and the third set of filters is located on an opposite side of the imaging optics.

3. The system of claim 2, wherein the third set of filters comprises a dichroic filter.

4. The system of claim 2, wherein the third set of filters is located on a filter wheel comprising at least one additional set of filters.

5. The system of claim 1, wherein rejection performance of the first set of filters matches rejection performance of the second set of filters.

6. The system of claim 1 further comprising a dichroic splitter between the light source and the detector, the dichroic splitter positioned such that light from the light source illuminates a target and light emitted from the target reaches the detector.

7. The system of claim 1 further comprising one or more additional light sources.

8. A detector system comprising:
a light detector;
imaging optics;
a set of filters positioned between the light detector and the imaging optics; and
an aperture located at a front focal plane of the imaging optics, wherein a telecentric space is created between the light detector and the imaging optics, such that axial rays from a plurality of field points emerge from the imaging optics parallel to each other and perpendicular to the set of filters.

9. A detector system comprising:
a light detector;
imaging optics;
a set of filters positioned between the light detector and the imaging optics;
an aperture located at a front focal plane of the imaging optics, wherein a telecentric space is created between the light detector and the imaging optics, such that axial rays from a plurality of field points emerge from the imaging optics parallel to each other and perpendicular to the set of filter; and
a second set of filters, wherein the set of filters is located on one side of the imaging optics and the second set of filters is located on an opposite side of the imaging optics.

10. The detector system of claim 9, wherein the second set of filters comprises a dichroic filter.

11. The detector system of claim 9, wherein the second set of filters is located on a filter wheel comprising at least one additional set of filters.

12. A detector system comprising:
a light detector;
imaging optics;
a set of filters positioned between the light detector and the imaging optics;
an aperture located at a front focal plane of the imaging optics, wherein a telecentric space is created between the light detector and the imaging optics, such that axial rays from a plurality of field points emerge from the imaging optics parallel to each other and perpendicular to the set of filter; and wherein the set of filters is designed to pass wavelengths of light in an emission band of a fluorescent material.

13. A method for fluorescence filtering, the method comprising:
(a) illuminating a target comprising a fluorescent material with light in an absorption band of the fluorescent material, wherein, in response to absorbing the light in the absorption band, the fluorescent material emits light in an emission band of the fluorescent material;
(b) causing axial rays of light beams from a plurality of field points in the target to emerge from imaging optics parallel to each other and perpendicular to a set of filters designed to pass wavelengths of light in the emission band; and
(c) detecting light passed through the set of filters.

14. The method of claim 13 further comprising, before (a), passing light from a light source through a set of filters designed to pass light in the absorption band.

15. The method of claim 14, wherein rejection performance of the set of filters designed to pass wavelengths of light in the emission band matches rejection performance of the set of filters designed to pass wavelengths of light in the absorption band.

16. The method of claim 13 further comprising, between (a) and (b), passing light emitted from the fluorescent material through a second set of filters designed to pass wavelengths of light in the emission band.

17. The method of claim 16, wherein the second set of filters comprises a dichroic filter.

18. The method of claim 16, wherein the second set of filters are located on a filter wheel comprising at least one additional set of filters.

19. The method of claim 13, wherein (a) is performed by a single light source.

20. The method of claim 13, wherein (a) is performed by two or more light sources.

21. The system of claim 1, wherein the source subsystem comprises one or more additional sets of filters.

22. A detector system comprising:

a light detector;

imaging optics;

a set of filters positioned between the light detector and the imaging optics; and an aperture located at a front focal plane of the imaging optics, wherein a telecentric space is created between the light detector and the imaging optics, such that axial rays from a plurality of field points emerge from the imaging optics parallel to each other and perpendicular to the set of filters and wherein the axial rays impinge upon the detector parallel to each other and perpendicular to the detector.

* * * * *

UNITED STATES PATENT AND TRADEMARK OFFICE
CERTIFICATE OF CORRECTION

PATENT NO. : 7,286,232 B2
APPLICATION NO. : 11/355848
DATED : October 23, 2007
INVENTOR(S) : Ahmed Bouzid It is certified that error appears in the above-identified patent and that said Letters Patent is hereby corrected as shown below:

In the Claims

Col. 8, Claim 1, Line 3: delete "a" before "the".

Signed and Sealed this
Fourteenth Day of October, 2014

Michelle K. Lee
*Deputy Director of the United States Patent and Trademark Office*